United States Patent
Wilk

(10) Patent No.: US 7,879,050 B2
(45) Date of Patent: Feb. 1, 2011

(54) TRANS-VASCULAR SURGICAL METHOD AND ASSOCIATED DEVICE

(76) Inventor: Peter J. Wilk, 475 E. 72$^{nd}$ St., Suite 1L, New York, NY (US) 10021

( * ) Notice: Subject to any disclaimer, the term of this patent is extended or adjusted under 35 U.S.C. 154(b) by 791 days.

(21) Appl. No.: 11/369,618

(22) Filed: Mar. 7, 2006

(65) Prior Publication Data
US 2006/0217595 A1 Sep. 28, 2006

Related U.S. Application Data

(60) Provisional application No. 60/664,357, filed on Mar. 23, 2005.

(51) Int. Cl.
*A61B 17/04* (2006.01)
(52) U.S. Cl. .................. 606/148; 606/151; 606/157
(58) Field of Classification Search .............. 606/157, 606/158, 213, 214, 135; 600/207; 128/831, 128/843, 898
See application file for complete search history.

(56) References Cited

U.S. PATENT DOCUMENTS

| | | | |
|---|---|---|---|
| 4,610,665 A | | 9/1986 | Matsumoto et al. |
| 5,273,051 A | | 12/1993 | Wilk |
| 5,297,536 A | | 3/1994 | Wilk |
| 5,458,131 A | | 10/1995 | Wilk |
| 5,571,167 A | * | 11/1996 | Maginot .................. 128/898 |
| 5,676,671 A | | 10/1997 | Inoue |
| 5,980,567 A | | 11/1999 | Jordan |
| 6,027,520 A | * | 2/2000 | Tsugita et al. ............ 606/200 |
| 6,068,638 A | * | 5/2000 | Makower .................. 606/159 |
| 6,217,554 B1 | * | 4/2001 | Green ................... 604/164.01 |
| 6,409,751 B1 | * | 6/2002 | Hall et al. ................. 623/1.11 |
| 6,440,061 B1 | * | 8/2002 | Wenner et al. ............. 600/114 |
| 6,464,665 B1 | | 10/2002 | Heuser |
| 6,629,951 B2 | * | 10/2003 | Laufer et al. ............ 604/96.01 |
| 6,692,458 B2 | | 2/2004 | Forman et al. |
| 6,802,806 B2 | | 10/2004 | McCarthy et al. |
| 7,442,184 B2 | * | 10/2008 | Katoh et al. ............ 604/96.01 |
| 2001/0049497 A1 | | 12/2001 | Kalloo et al. |
| 2004/0186507 A1 | * | 9/2004 | Hall et al. ................. 606/194 |
| 2006/0241244 A1 | * | 10/2006 | Soeda et al. ............... 525/178 |
| 2006/0241344 A1 | * | 10/2006 | Wilk ......................... 600/114 |

FOREIGN PATENT DOCUMENTS

WO WO99/62408 * 12/1999

* cited by examiner

*Primary Examiner*—(Jackie) Tan-Uyen T Ho
*Assistant Examiner*—Alexander Orkin
(74) *Attorney, Agent, or Firm*—R. Neil Sudol; Henry D. Coleman; William J. Sapone

(57) ABSTRACT

A trans-vascular surgical method includes forming an artificial opening in a blood vessel of a patient's vascular system at a substantially predetermined location and moving a distal end portion of a medical instrument through at least a section of the patient's vascular system and through the artificial opening. A surgical port device is disposed inside the blood vessel to inhibit blood from exiting the patient's vascular system through the artificial opening while permitting extension of the distal end portion of the medical instrument through the artificial opening. After moving the distal end portion of the medical instrument through the artificial opening, the medical instrument is operated to perform a medical procedure operation inside the patient.

14 Claims, 4 Drawing Sheets

TRANS-VASCULAR SURGICAL METHOD AND ASSOCIATED DEVICE

CROSS-REFERENCE TO RELATED APPLICATION

This application claims the benefit of U.S. Provisional Patent Application No. 60/664,357 filed Mar. 23, 2005.

BACKGROUND OF THE INVENTION

This invention relates to a medical surgical procedure. More particularly, this invention relates to a minimally invasive surgical method. This invention also relates to a surgical port device and instrument kit for use in carrying out the method.

U.S. Pat. Nos. 5,297,536 and 5,458,131 disclose a minimally invasive method for intra-abdominal surgical procedures that avoids the formation of an incision in the patient's skin surface. As described in those patents, a method for use in intra-abdominal surgery comprises the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

Visual feedback may be obtained as to position of a distal end of the incising instrument prior to the manipulating thereof to form the perforation. That visual feedback may be obtained via the endoscope or, alternatively, via radiographic or X-ray equipment.

The abdominal cavity may be insufflated prior to the insertion of the distal end of the endoscope into the abdominal cavity. Insufflation may be implemented via a Veress needle inserted through the abdominal wall or through another perforation in the internal wall of the natural body cavity. That other perforation is formed by the Veress needle itself. U.S. Pat. No. 5,209,721 discloses a Veress needle that utilizes ultrasound to detect the presence of an organ along an inner surface of the abdominal wall.

A method in accordance with the disclosures of U.S. Pat. Nos. 5,297,536 and 5,458,131 comprises the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

The surgical procedures of U.S. Pat. Nos. 5,297,536 and 5,458,131 reduce trauma to the individual even more than laparoscopic procedures. Hospital convalescence stays are even shorter. There are some potential problems with the procedures, such as the difficulty in forming a fluid tight closure of the perforation formed in the wall of the hollow internal body organ. Certain intra-abdominal operations cannot be easily performed owing to the necessity or removing large chunks of organic or inorganic material (e.g., entire kidney, gall stones). Some operations can require the simultaneous usage of many different instruments so that space along the selected pathways may be difficult to find.

U.S. Pat. No. 5,273,051 describes a minimally invasive method that provides access to abdominal organs via the vascular system, for purposes obtaining a biopsy of an internal organ. The method of that patent more particularly comprises the steps of (a) providing a biopsy device including a flexible elongate tubular member and a biopsy-taking component at a distal end of the tubular member for obtaining a tissue sample, (b) forming an incision in a blood vessel of a vascular system of the patient, (c) inserting a distal end portion of the biopsy device through the incision into the blood vessel, (d) manipulating the biopsy device to maneuver the distal end portion through the vascular system to the internal organ, (e) piercing a blood vessel wall with a sharp distal tip of the biopsy device upon arrival of the biopsy-taking component at the internal organ, (f) pushing the biopsy device so that the biopsy-taking component enters the internal organ, (g) operating the biopsy-taking component to capture a sample of tissues of the internal organ, and (h) withdrawing the biopsy device with the captured tissue sample from the vascular system of the patient through the blood vessel and the incision.

OBJECTS OF THE INVENTION

It is an object of the present invention to provide a minimally invasive method for obtaining access to internal organs of a patient.

Another object of the present invention is to provide such a method that utilizes the vascular system of the patient.

It is a more particular object of the present invention to provide such a method that permits access to external surfaces of internal organs.

A further object of the present invention is to provide a surgical device that facilitates the performance of a surgical method in accordance with the invention.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

A surgical method in accordance with the present invention comprises forming an artificial opening in a blood vessel of a patient's vascular system at a substantially predetermined location, moving a distal end portion of a medical instrument through at least a section of the patient's vascular system and through the artificial opening, disposing a surgical port device inside the blood vessel to inhibit blood from exiting the patient's vascular system through the artificial opening while permitting extension of the distal end portion of the medical instrument through the artificial opening, and after moving the distal end portion of the medical instrument through the artificial opening, operating the medical instrument to perform a medical procedure operation inside the patient.

The surgical method may additionally comprise withdrawing the distal end of the medical instrument back into the patient's vascular system through the artificial opening after the performance of the medical procedure and closing the artificial opening after the withdrawing of the medical instrument.

The closing of the artificial opening may include applying a patch to an endothelial surface of the blood vessel at the predetermined location in a region about the artificial opening. The patch may take a tubular shape. The patch may include barbs or hooks along a surface in contact with the endothelial surface, for purposes of securing the patch to the endothelial surface.

Pursuant to another feature of the present invention, the port device includes a valve element and the inserting of the distal end portion of the medical instrument includes engaging an outer surface of the medical instrument with the valve element to form a seal about the medical instrument. The valve element may take the specific form of a membrane having an aperture.

Where a surgical site in accordance with the present invention is located in an internal space such as the abdominal cavity, the method may further comprise introducing a pressurized gas into the internal space via an elongate tube communicating with the internal space via the port device.

The invention contemplates that the distal end portion of the medical instrument is moved through the artificial opening after disposition of the port device in the blood vessel. In addition, the deployment of a surgical incising tool for forming the artificial opening in the vessel wall may occur after disposition of the port device in the blood vessel. Where the port device includes a guide surface and the port device is disposed at the predetermined location in the vascular system, the moving of the medical instrument through the artificial opening includes deflecting the distal end portion of the medical instrument through the artificial opening by engaging the distal end portion of the medical instrument with the guide surface. The guide surface may take the form of a curved cylindrical section that deflects the advancing instrument shaft in a camming action.

The forming of the artificial opening may include inserting a distal end portion of a surgical instrument into the patient's vascular system, moving the distal end portion of the surgical instrument through a section of the patient's vascular system to the blood vessel, and manipulating the surgical instrument from outside the patient to form the artificial opening.

Where the port device includes a balloon element, the disposing of the port device includes shifting the port device through a section of the patient's vascular system to the predetermined location. The balloon element is in a collapsed configuration during the shifting of the port device. The disposing of the port device further includes inflating the balloon element after arrival of the port device at the predetermined location.

A surgical port device in accordance with the present invention comprises a body or frame member and a deflection or guide element attached to the body or frame member for directing an intravascular instrument through a wall of the blood vessel.

Pursuant to another feature of the present invention, the body or frame member includes a balloon that is expandable to an inflated configuration for occluding a lumen of a blood vessel. The inflated configuration of the balloon preferably has an annular outer surface for facilitating a fluid-tight engagement with the endothelial surface of the vessel.

The balloon may be one of a pair of balloons located at opposite ends of the body or frame member. An elongate tube may extend to the port device and communicate with the balloon(s) for inflating the same from a collapsed configuration to an expanded configuration.

The present invention provides a minimally invasive surgical method that is particularly useful for certain kinds of abdominal interventions. For example, a Fallopian tube ligation can be effectively performed by inserting the operating head of a clip applier through the femoral vein and the iliac vein and out of the vascular system into the abdominal cavity through the sub-iliac vein. Although one can perform certain trans-vascular surgical operations in accordance with the present invention via the arterial subsystem, the venous subsystem is the preferred route for most inventions.

A surgical instrument kit in accordance with the present invention comprises a first medical instrument insertable percutaneously into a patient's vascular system and operable to form an artificial opening in a blood vessel of the patient's vascular system at a substantially predetermined location, a second medical instrument insertable percutaneously into the patient's vascular system, through at least a section of the patient's vascular system and through the artificial opening, and a surgical port device disposable inside the blood vessel to inhibit blood from exiting the patient's vascular system through the artificial opening while permitting extension of the distal end portion of second the medical instrument through the artificial opening.

The kit defined may further comprise a patch applicable to an endothelial surface of the blood vessel at the predetermined location in a region about the artificial opening.

The port device may include a valve element such as an annular membrane engageable with an outer surface of the second medical instrument with to form a seal about the second medical instrument. The kit may additionally comprise an elongate tube attached to and extending at least partially through the port device for delivering a pressurized gas into the internal space.

The port device may include a balloon element and a guide surface for deflecting the distal end portion of the medical instrument during insertion thereof through the artificial opening.

DETAILED DESCRIPTION

Figure 1:
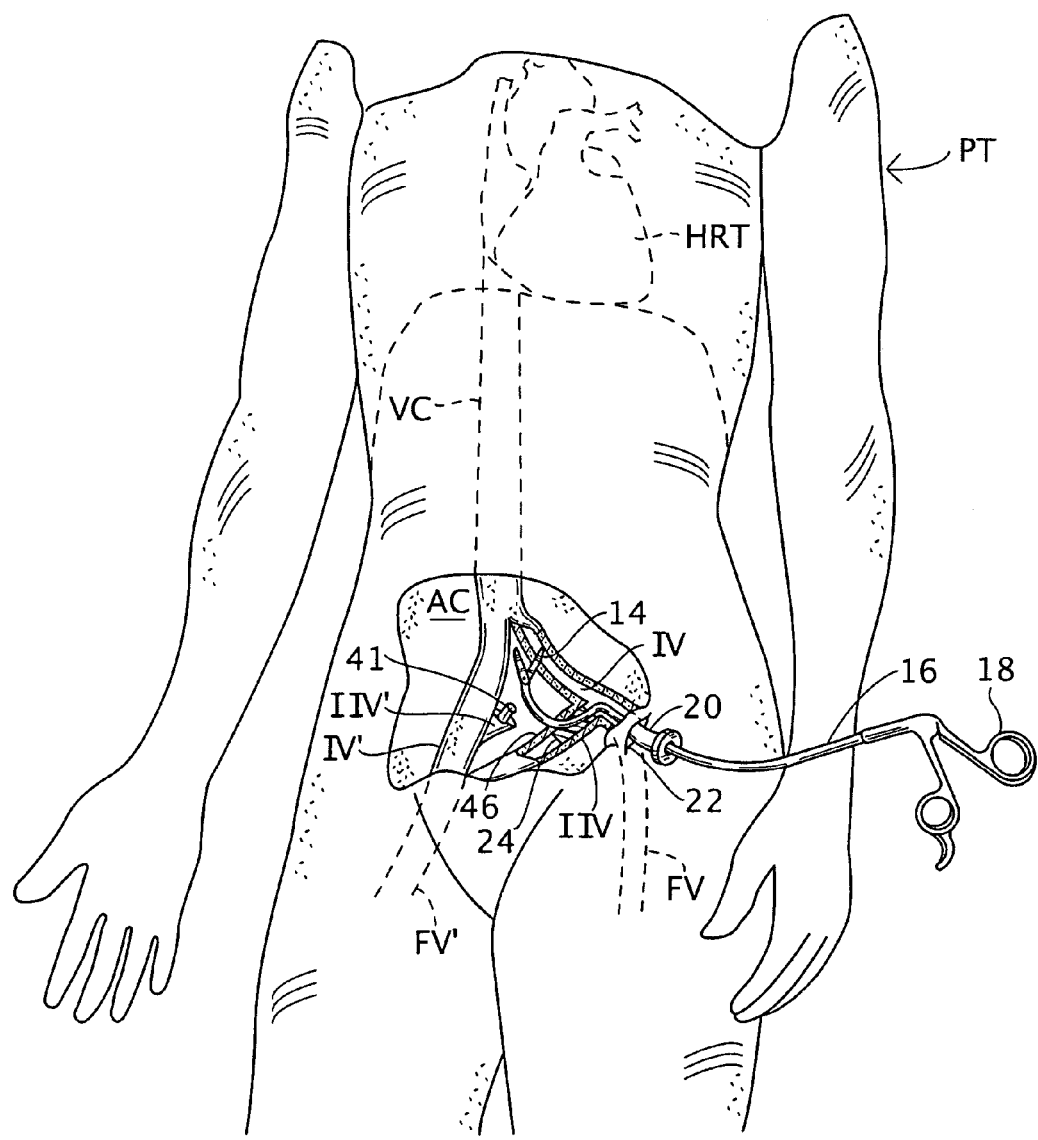
FIG. 1 is a schematic view of a human patient, showing deployment of a medical instrument in a surgical procedure in accordance with the present invention.

FIG. 1 depicts a stage in a minimally invasive surgical method wherein access in obtained to an internal space such as the abdominal cavity AC via the patient's vascular system. A medical instrument 12 such as a surgical forceps having an operative tip 14, an elongate flexible shaft 16 and an actuator handle 18 is inserted through an external port element 20 into a femoral vein FV. A distal end portion (not separately designated) of medical instrument 12 is steerable from handle 18 (steering knobs not shown) to enable a wending of the distal end portion from femoral vein FV into the respective iliac vein IV and from there into the respective internal iliac vein IIV. Iliac vein IV channels blood from femoral vein FV to the vena cava VC and then to the heart HRT.

Figure 2:
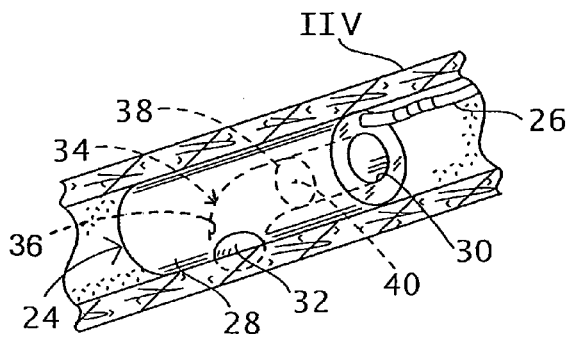
FIG. 2 is a schematic cross-sectional view of a vein, showing a surgical port device deployed therein, in accordance with the present invention.

Prior to the insertion of medical instrument 12, an incision 22 is made in a thigh TH of the patient PT to the femoral vein FV. External port element 20 is then installed in the incision 22. Subsequently, an internal port device 24 as illustrated in FIG. 2 is inserted into femoral vein FV via port element 20 and pushed through iliac vein IV and into internal iliac vein IIV to a predetermined location along the internal iliac vein IIV inside the patient's abdominal cavity AC. Port device 24 may be connected to a distal end of a steerable guide wire 26 for purposes of deployment. During a subsequent trans-vascular surgical operation, guide wire 26 may remain connected to port device 24, in part for facilitating removal of port device 24 after completion of the trans-vascular operation.

Surgical port device 24 comprises a body or frame member 28 with an opening 30 at a proximal end, an opening 32 in a cylindrical sidewall, and a channel 34 extending between the two openings. Channel 34 includes a curved elbow surface 36 that functions as a deflector or guide surface for turning medical instrument 12 (FIGS. 1 and 3) from a longitudinal orientation to a transverse orientation as the medical instrument is pushed in the distal direction from outside the patient PT. Channel 34 may be provided internally with a valve element 38 in the form of a self-sealing membrane in turn provided with a perforation 40 for enabling passage of medical instrument 12. The membrane valve 38 engages an outer surface of medical instrument 12 to form a seal about the medical instrument.

Port device 24 and medical instrument 12, as well as other surgical armamentarium, may be deployed using techniques common to percutaneous intravascular procedures. In particular, guide wire technology and visualization methods used in those procedures are utilizable in the present procedures. FIG. 1 schematically depicts a method for visual feedback wherein a distal end of a flexible endoscope 41 is inserted into the abdominal cavity via another route through the patient's vascular system, exemplarily including the other femoral vein FV', the other iliac vein IV', and the other internal iliac vein IIV'.

After the placement of port device 24 at a substantially predetermined location in a blood vessel such as internal iliac vein IIV, a surgical incising instrument 42 is inserted through external port element 20 and guided to internal port device 24. Incising instrument 42 is then pushed further in a distal direction so that an operative tip 44 enters channel 34 and is turned by deflection surface 36 towards a wall of the blood vessel IIV (see FIG. 3). Incising instrument 42 is then actuated from outside the patient PT to form an artificial opening 46 in the internal iliac vein IIV. After the formation of incision or artificial opening 46, incising instrument 42 is withdrawn from the patient PT and medical instrument 12 is inserted, as illustrated in FIG. 4.

Figure 3:
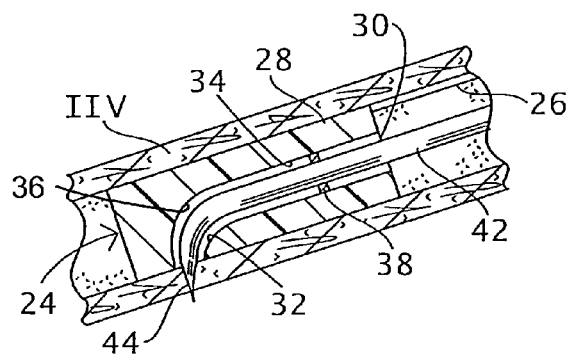
FIG. 3 is a view similar to FIG. 2, showing the port device in cross-section, as well as an incising instrument, in accordance with the present invention.
Figure 4:
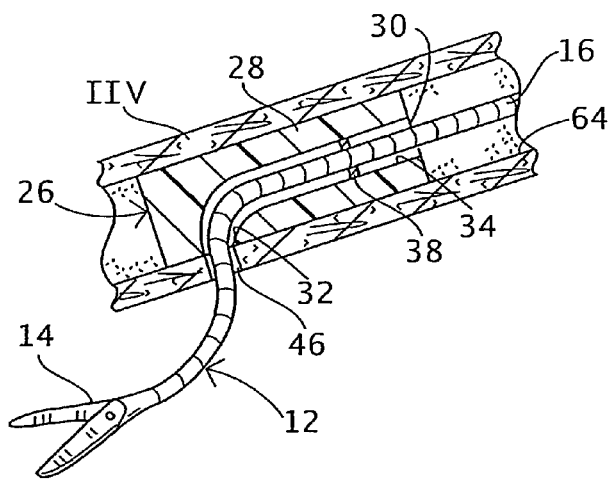
FIG. 4 is a view similar to FIGS. 2 and 3, on a larger scale, showing the port device in cross-section, as well as a surgical instrument inserted through the vein wall, in accordance with the present invention.
Figure 5:
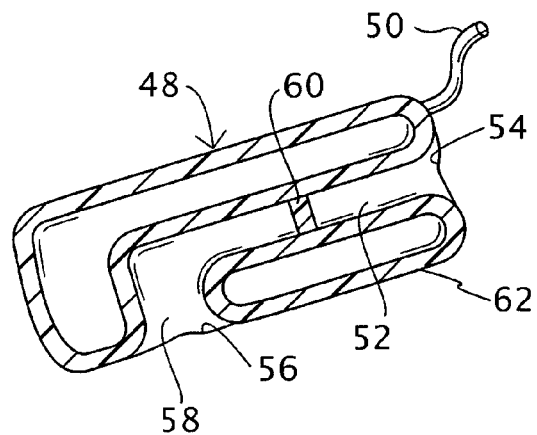
FIG. 5 is a longitudinal cross-sectional view of another surgical port device in accordance with the present invention, for use in performing the method of the invention.

Port device 24 may be a solid polymeric body or frame element as illustrated in FIGS. 3 and 4 or have a body element in the form of a balloon 48, as illustrated in FIG. 5. An inflation tube 50 is connected to balloon 48 for guiding a fluid thereto to expand the balloon from a collapsed insertion configuration (not shown) to the inflated use configuration illustrated in FIG. 5. Tube 50 may be incorporated in or attached to guide wire 26 (FIG. 2). In the former case, guide wire 26 takes the form of a cable that has an internal longitudinal channel or lumen. As discussed above with respect to port device 24, balloon 48 has a channel 52 extending from a proximal opening 54 to a lateral opening 56 in the sidewall of the balloon. Channel 52 has a curved inner surface 58 that serves to deflect incoming medical instruments from a longitudinal path of movement to a path transverse to the blood vessel, e.g., internal iliac vein IIV. Balloon 48 has a valve element 60 in the form of a self-sealing membrane that extends across the channel 52, exemplarily at lateral opening 56. The membrane valve 60 engages an outer surface of medical instrument 12 (or 42) to form a seal about the medical instrument.

Balloon 48 is expandable to its inflated configuration for occluding a lumen of blood vessel IIV. The inflated configuration of balloon 48 preferably has an annular outer surface 62 for facilitating a fluid-tight engagement with the endothelial inner surface 64 (FIG. 4) of the blood vessel IIV at the access site.

Figure 6:
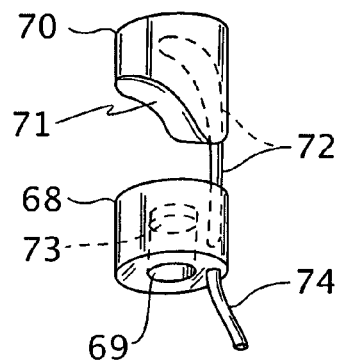
FIG. 6 is a schematic perspective view of another surgical port device in accordance with the present invention, for use in performing the method of the invention.

As illustrated in FIG. 6, an intravascular port device 66 for use in the present method may comprise a pair of balloons 68 and 70 located at opposite ends of a body or frame member 72 such as a hollow rod. An elongate tube 74 extends to port device 66 and communicates with balloons 68 and 70 for inflating the same from a collapsed configuration to an expanded configuration after the device has been moved to a predetermined site for penetration from the vascular system into the abdominal cavity AC (or other space within the patient PT). Balloon 68 is provided with a through-opening or channel 69, while balloon 70 is formed with a curved deflection or guide surface 71. Channel 69 may be provided with a self-sealing membrane valve element 73.

Port devices 24, 48 and 66 inhibit blood from exiting the patient's vascular system through artificial opening 46 while permitting extension of the distal end portion of medical instrument 12 through the artificial opening. After moving the distal end portion of the medical instrument 12 through the artificial opening, the surgeon operates the medical instrument to perform a medical procedure operation inside the patient PT and more particularly in the abdominal cavity AC of the patient.

Figure 7A:
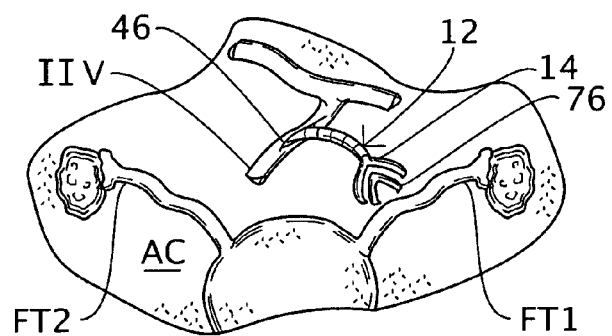
FIGS. 7A-7C are schematic cross-sectional views of a woman's abdomen, showing successive steps in a trans-vascular medical procedure in accordance with the present invention.
Figure 7B:
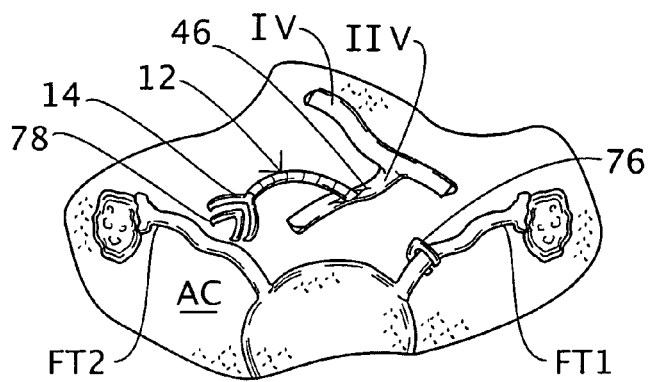
Figure 7C:
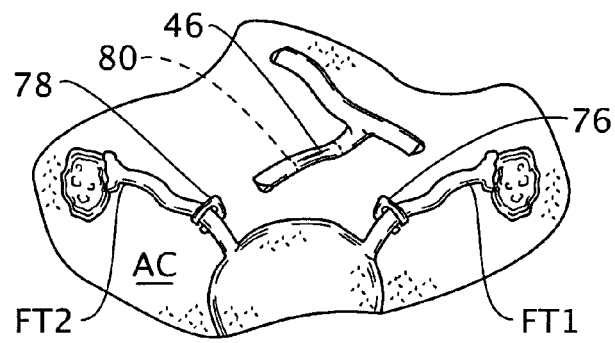
Figure 8:
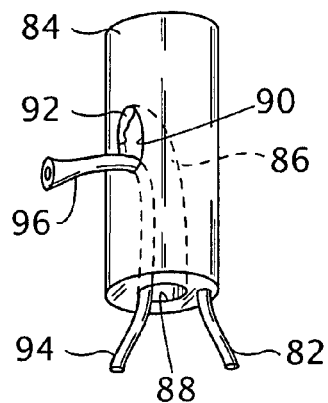
FIG. 8 is a view similar to FIG. 6, showing yet another surgical port device in accordance with the present invention, for use in performing the method of the invention.

FIGS. 7A-7C depict stages of a tubal ligation procedure conducted via the vascular system and the abdominal cavity AC. As discussed above, a medical instrument 12 in the form of a clip applier is inserted into the abdominal cavity via incision 46 made in internal iliac vein IIV. Clip applier 12 is manipulated from outside the patient to place a first clip 76 about one Fallopian tube FT1 and a second clip 78 about the other Fallopian tube FT2. The distal end portion of clip applier 12 is withdrawn back into the patient's vascular system through artificial opening 46 after the performance of the tubal ligation procedure. Artificial opening 46 is then closed, for example, by applying a tubular adhesive patch 80 to the lumen of internal iliac vein IIV. Patch 80 may be provided with a plurality of barbs or hooks (not shown) along a surface in contact with the endothelial surface of the vein IIV. The barbs or hooks serve to secure the patch 80 to the endothelial tissue.

Where a surgical site in accordance with the present invention is located in an internal space such as the abdominal cavity AC, the method may further comprise introducing a pressurized gas into the internal space via an elongate tube 82 communicating with the internal space via a surgical port device 84 as depicted in FIG. 8. Port device 84 includes a channel 86 extending from an inlet opening 88 to an outlet 90 covered with a membrane seal 92. A tube 94 for conveying carbon dioxide gas to abdominal cavity AC for purposes of maintaining pneumoperitoneum is connected to port device 84. A distal end 96 of tube 94 extends through seal 92 and is insertable into the abdominal cavity, for instance, with the aid of a forceps or graspers (not illustrated).

The surgical tools, instruments and closure elements described hereinabove may be provided in various combinations as kits for facilitating not only the distribution of the surgical tools, instruments and closure elements but also the deployment and utilization of the surgical tools, instruments and closure elements in the operating room.

Although the invention has been described in terms of particular embodiments and applications, one of ordinary skill in the art, in light of this teaching, can generate additional embodiments and modifications without departing from the spirit of or exceeding the scope of the claimed invention. For example, in some cases, a trans-vascular intervention in the abdominal cavity or other internal space may be effectuated without an intra-vascular port device at the site of penetration from the vascular system into the internal space. In that case surgical instruments are directed out of the vascular system through the artificial opening in the vascular wall by steering the instrument head from outside the patient. An endoscope may be inserted into the vascular system via port element 20 for purposes of providing feedback to inform the operating surgeon as to conditions at the site of incision 46. Accordingly, it is to be understood that the drawings and descriptions herein are proffered by way of example to facilitate comprehension of the invention and should not be construed to limit the scope thereof.

What is claimed is:

1. A surgical method comprising:
   forming an artificial opening in a blood vessel of a patient's vascular system at a substantially predetermined location in the abdominal cavity;
   moving a distal end portion of a medical instrument through at least a section of the patient's vascular system and through said artificial opening and into the abdominal cavity;
   after moving the distal end portion of said medical instrument through said artificial opening, operating said medical instrument to perform a medical procedure in the abdominal cavity; and
   introducing a pressurized gas into said internal space to maintain pneumoperitoneum therein.

2. The surgical method defined in claim 1, further comprising:
   after the performance of said medical procedure, withdrawing the distal end of said medical instrument back into the patient's vascular system through said artificial opening; and
   after the withdrawing of said medical instrument, closing said artificial opening and removing said surgical port device from said blood vessel.

3. The surgical method defined in claim 2 wherein the closing of said artificial opening includes applying a patch to an endothelial surface of the blood vessel at said predetermined location in a region about said artificial opening.

4. The surgical method defined in claim 1, further comprising:
   after the performance of said medical procedure, withdrawing the distal end of said medical instrument back into the patient's vascular system through said artificial opening; and
   after the withdrawing of said medical instrument, closing said artificial opening.

5. The surgical method defined in claim 4 wherein the closing of said artificial opening includes applying a patch to an endothelial surface of the blood vessel at said predetermined location in a region about said artificial opening.

6. The surgical method defined in claim 1, further comprising disposing a surgical port device inside the blood vessel to inhibit blood from exiting the patient's vascular system through said artificial opening while permitting extension of the distal end portion of said medical instrument through said artificial opening, wherein said port device includes a valve element, the inserting of said distal end portion of said medical instrument including engaging an outer surface of said medical instrument with said valve element to form a seal about said medical instrument.

7. The surgical method defined in claim 1 wherein the forming of said artificial opening includes:
   inserting a distal end portion of a surgical instrument into a blood vessel at another location in the patient's vascular system;
   moving the distal end portion of said surgical instrument through a section of the patient's vascular system to said predetermined location in the patient's vascular system; and
   manipulating said surgical instrument from outside the patient to form said artificial opening.

8. The surgical method defined in claim 1, further comprising disposing a surgical port device inside the blood vessel to inhibit blood from exiting the patient's vascular, system through said artificial opening while permitting extension of the distal end portion of said medical instrument through said artificial opening, wherein said port device includes a balloon element, the disposing of said port device including shifting said port device through a section of the patient's vascular system to said blood vessel, said balloon element being in a collapsed configuration during the shifting of said port device, the disposing of said port device further including inflating said balloon element after arrival of said port device in said blood vessel so that said port device is in fluid-tight engagement with the endothelial surface of said blood vessel all around an internal circumference of said blood vessel.

9. The method defined in claim 1 wherein said blood vessel is a vein.

10. The surgical method defined in claim 1 wherein the introducing of said pressurized gas is carried out via an elongate tube communicating with the abdominal cavity via said artificial opening.

11. A surgical method comprising:
   forming an artificial opening in a blood vessel of a patient's vascular system at a substantially predetermined location in the abdominal cavity;

moving a distal end portion of an elongate tube through at least a section of the patient's vascular system and at least partially through said artificial opening to the abdominal cavity; and introducing a pressurized gas into the abdominal cavity via said elongate tube to maintain pneumoperitoneum in the abdominal cavity.

12. The surgical method defined in claim 11, further comprising disposing a surgical port device inside the blood vessel to inhibit blood from exiting the patient's vascular system through said artificial opening while permitting communication of the distal end portion of said elongate tube with the abdominal cavity through said artificial opening.

13. The surgical method defined in claim 12 wherein said elongate tube extends through said port device.

14. The surgical method defined in claim 12 wherein said port device includes a balloon element, the disposing of said port device including shifting said port device through a section of the patient's vascular system to said blood vessel, said balloon element being in a collapsed configuration during the shifting of said port device, the disposing of said port device further including inflating said balloon element after arrival of said port device in said blood vessel so that said port device is in fluid-tight engagement with the endothelial surface of said blood vessel all around an internal circumference of said blood vessel.

* * * * *